(12) United States Patent
Dakka et al.

(10) Patent No.: US 7,579,511 B1
(45) Date of Patent: Aug. 25, 2009

(54) PROCESS FOR MAKING CYCLOHEXYLBENZENE

(75) Inventors: Jihad Mohammed Dakka, Whitehouse Station, NJ (US); Lorenzo Cophard DeCaul, Langhorne, PA (US); Teng Xu, Hampton, NJ (US)

(73) Assignee: Exxonmobil Research and Engineering Company, Annadale, NJ (US)

( * ) Notice: Subject to any disclaimer, the term of this patent is extended or adjusted under 35 U.S.C. 154(b) by 0 days.

(21) Appl. No.: 12/287,655

(22) Filed: Oct. 10, 2008

(51) Int. Cl.
*C07C 2/64* (2006.01)
*C07C 2/66* (2006.01)

(52) U.S. Cl. .................. 585/316; 585/314; 585/318; 585/319; 585/320; 585/323

(58) Field of Classification Search ............ 585/316, 585/314, 315, 318, 319, 320, 323
See application file for complete search history.

(56) References Cited

U.S. PATENT DOCUMENTS

| | | |
|---|---|---|
| 3,962,362 A | 6/1976 | Suggitt |
| 4,094,918 A | 6/1978 | Murtha et al. |
| 4,122,125 A | 10/1978 | Murtha et al. |
| 4,177,165 A | 12/1979 | Murtha et al. |
| 4,206,082 A | 6/1980 | Murtha et al. |
| 5,053,571 A | 10/1991 | Makkee |
| 6,037,513 A | 3/2000 | Chang et al. |
| 6,489,529 B1 | 12/2002 | Cheng et al. |

FOREIGN PATENT DOCUMENTS

CS 177505 7/1977

OTHER PUBLICATIONS

U.S. Appl. No. 61/047,821, filed Apr. 25, 2008, ExxonMobil Chemical Patents, Inc.
Neftekhimiya, V17, N. 5705-9, Sep.-Oct. 1977, "A Commercial Synthesis of Phenylcyclohexane ((PHCH)) by the Hydrodimerization of Benzene".

*Primary Examiner*—Thuan Dinh Dang
(74) *Attorney, Agent, or Firm*—Robert A. Migliorini

(57) ABSTRACT

Provided is a process for making cyclohexylbenzene. The process includes the following steps: (a) contacting benzene and hydrogen in the presence of a first catalyst under hydroalkylation conditions sufficient to form a first effluent stream having cyclohexylbenzene, cyclohexane, methyl cyclopentane, and unreacted benzene; (b) supplying at least part of said first effluent stream to a first separation system to divide said first effluent stream part into a cyclohexane/methylcyclopentane-rich stream, a cyclohexane-rich stream, a benzene-rich stream, and a dicyclohexyl benzene-rich stream; (c) recycling at least part of the benzene-rich stream to the contacting step (a); (d) contacting the cyclohexane/methylcyclopentane-rich stream with a second catalyst that catalyzes dehydrogenation and exhibits low acidity under conditions sufficient to convert at least a portion of the cyclohexane to benzene and at least a portion of the methylcyclopentane to linear and/or branched paraffins to form a second effluent stream; and (e) recycling at least part of the second effluent stream to the contacting step (a).

9 Claims, 2 Drawing Sheets

PROCESS FOR MAKING CYCLOHEXYLBENZENE

FIELD

The present disclosure relates to a process for making cyclohexylbenzene.

BACKGROUND

Cyclohexylbenzene can be produced from benzene by the process of hydroalkylation or reductive alkylation. Benzene is heated with hydrogen in the presence of a catalyst such that the benzene undergoes partial hydrogenation to produce cyclohexene, which then alkylates the benzene to form cyclohexylbenzene.

U.S. Pat. Nos. 4,094,918 and 4,177,165 disclose hydroalkylation of aromatic hydrocarbons over catalysts of nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed are zeolites X and Y. In addition, U.S. Pat. No. 5,053,571 proposes the use of ruthenium and nickel supported on zeolite beta as an aromatic hydroalkylation catalyst. These processes have disadvantages of low selectivity to cyclohexylbenzene, particularly at economically viable benzene conversion rates, and large quantities of unwanted by-products, particularly cyclohexane and methylcyclopentane.

U.S. Pat. No. 6,037,513 discloses that cyclohexylbenzene selectivity in the hydroalkylation of benzene can be improved by contacting benzene and hydrogen with a bifunctional catalyst having at least one hydrogenation metal and a molecular sieve of the MCM-22 family. The hydrogenation metal is preferably selected from among palladium, ruthenium, nickel, cobalt and mixtures thereof, and the contacting step is conducted at a temperature of about 50° C. to 350° C., a pressure of about 100 to 7000 kPa, benzene to hydrogen molar ratio of about 0.01 to 100 and a WHSV of about 0.01 to 100. The '513 patent discloses that the cyclohexylbenzene can then be oxidized to the corresponding hydroperoxide and the peroxide cleaved to the desired phenol and cyclohexanone.

Although the use of MCM-22 family catalysts has afforded an increase in cyclohexylbenzene selectivity, significant amounts of cyclohexane and methyl cyclopentane are nonetheless produced. The conditions of low temperature (less than 200° C.) and high pressure (greater than 790 kPa) typically employed in hydroalkylation processes also favor the competing reaction of benzene reduction to cyclohexane. As a result, cyclohexane and methyl cyclopentane selectivities of 5 to 20 wt % are commonly observed. The production of cyclohexane and methyl cyclopentane results in the loss of valuable benzene feed and reduces the level of benzene conversion (typically 40 to 60 wt %), which necessitate recycle of unreacted benzene.

Cyclohexylbenzene can be formed by benzene alkylation with cyclohexene using MCM-22 family catalyst. Cyclohexene can be produced by selective partial benzene hydrogenation using homogenous and heterogeneous catalyst as described in many patents and articles (EP 323192, JP 85-204370, U.S. Pat. No. 4,055,512, DE 2520430). The major by products formed in the benzene hydrogenation are similar to the hydroalkylation process (cyclohexane and methylcyclopentane) therefore the invention concept could be used to solve the problems associated with the benzene hydrogenation.

Unless removed, cyclohexane and methyl cyclopentane build up in recycle streams, thereby displacing benzene and increasing the production of undesirable by-products. However, the similar boiling points of benzene, cyclohexane and methyl cyclopentane render separation difficult with conventional distillation. The hydroalkylation process and the various end products (and unreacted benzene) are shown in the following:

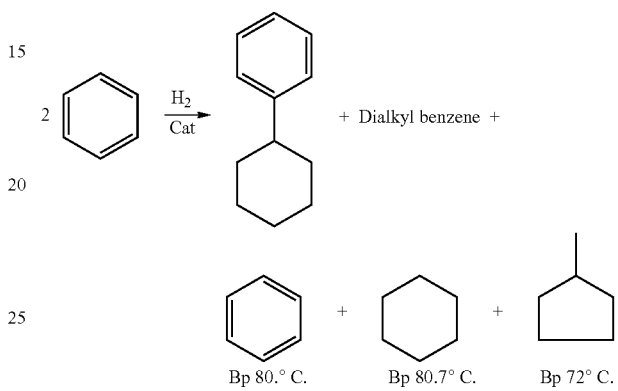

Moreover, during dehydrogenation of the recycle stream (dehydrogenation of cyclohexane by-product to benzene), methyl cyclopentane by-product forms methyl cyclopentadiene, a very reactive precursor for coke formation and an accelerator of catalyst deactivation.

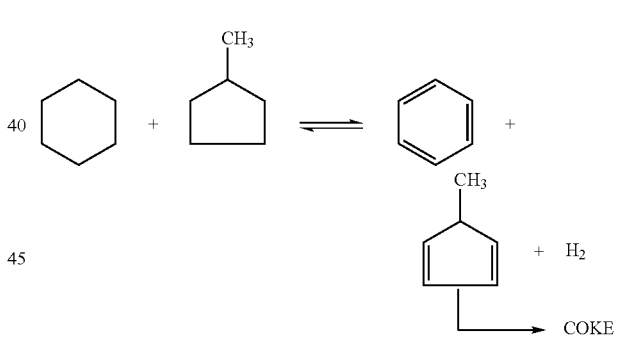

It would be desirable to have a process for hydroalkylating benzene affording enhanced conversion rates to cyclohexylbenzene. It would be further desirable to have a process wherein the build up of cyclohexane and methyl cyclopentane in recycle streams is reduced and the proportion of benzene therein is increased.

SUMMARY

According to the present disclosure, provided is a process for making cyclohexylbenzene. The process includes the following steps: (a) contacting benzene and hydrogen in the presence of a first catalyst under hydroalkylation conditions sufficient to form a first effluent stream having cyclohexylbenzene, cyclohexane, methyl cyclopentane, and unreacted benzene; (b) supplying at least part of said first effluent stream to a first separation system to divide said first effluent stream part into a cyclohexylbenzene-rich stream, a cyclohexane/ methylcyclopentane-rich stream, a benzene-rich stream, and a dicyclohexyl benzene-rich stream (the dicyclohexyl benzene-rich stream also having other heavy products); (c) recycling at least part of the benzene-rich stream to the contacting step (a); (d) contacting the cyclohexane/methylcyclopentane-rich stream with a second catalyst that catalyzes dehydrogenation and exhibits low acidity under conditions sufficient to convert at least a portion of the cyclohexane to benzene and at least a portion of the methylcyclopentane to linear and/or branched paraffins to form a second effluent stream; and (e) recycling at least part of the second effluent stream to the contacting step (a).

These and other features and attributes of the disclosed processes for making cyclohexylbenzene of the present disclosure and their advantageous applications and/or uses will be apparent from the detailed description which follows, particularly when read in conjunction with the figures appended hereto.

BRIEF DESCRIPTION OF THE DRAWINGS

To assist those of ordinary skill in the relevant art in making and using the subject matter hereof, reference is made to the appended drawings, wherein.

DETAILED DESCRIPTION OF THE INVENTION

Figure 1:
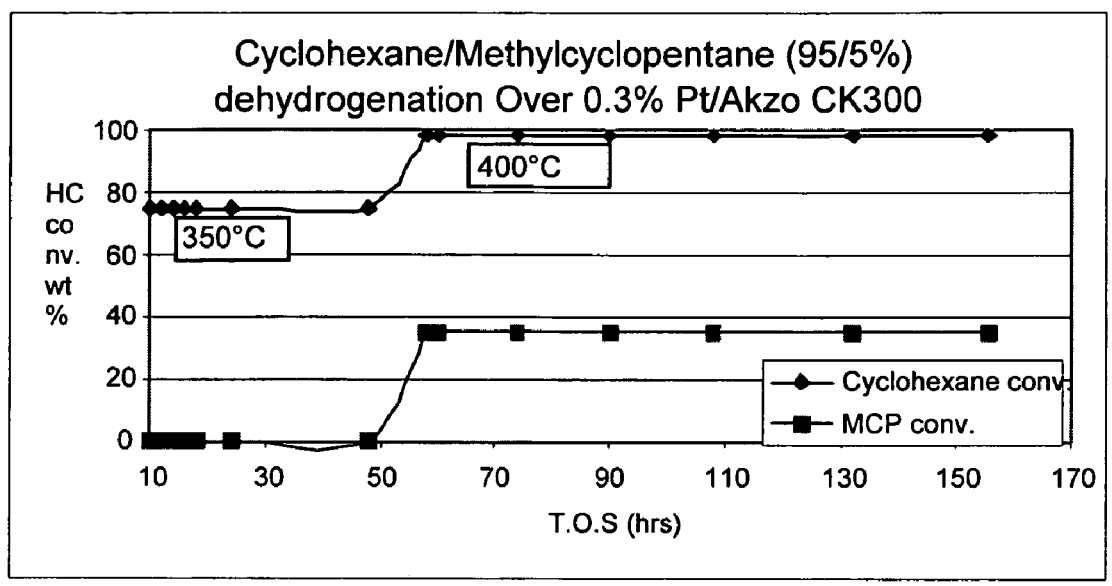
FIG. 1 is a plot showing cyclohexane and methyl cyclopentane conversion vs. T.O.S. at different temperature in Examples 10 and 11.
Figure 2:
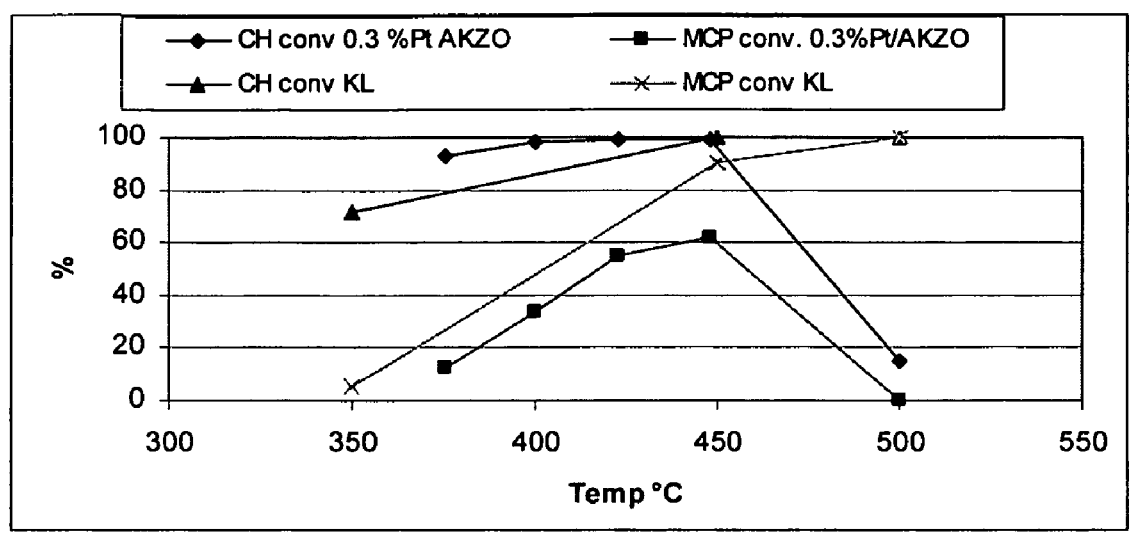
FIG. 2 is a plot showing catalyst stability as a function of reaction temperature in Examples 10 and 11.

All numerical values within the detailed description and the claims herein are modified by "about" or "approximately" the indicated value, and take into account experimental error and variations that would be expected by a person having ordinary skill in the art.

The problem of unwanted process by-products is alleviated by converting cyclohexane to benzene for recycle and methylcyclopentane to linear and/or branched paraffins for easier separation. The hydroalkylation effluent is contacted with a bifunctional catalyst having a dehydrogenation functionality and an acid functionality prior to recycle to the hydroalkylation reactor.

Any commercially available benzene and hydrogen feedstocks can be used in the present process. However, in hydroalkylation, it is desirable for the feedstocks to be as pure as possible. The sulfur, nitrogen, water, carbon monoxide and/or other impurities in the benzene feed and hydrogen feed may be removed by adsorption using 13X, 4A, Selexsorb CD, clay, Zn, Cu, and or any other effective adsorbents. The preferred sulfur level in the benzene feed to the hydroalkylation catalyst is less 5 wppm, generally less than 1 wppm. The preferred water level in the benzene feed is less than 500 wppm, generally less than 250 wppm. The preferred nitrogen level in the benzene feed is less than 1 wppm. Similarly, the preferred hydrogen sulfide level in the hydrogen feed is less than 5 wppm, generally less than 1 wppm. The preferred CO level in the hydrogen feed is also less than 5 wppm, generally less than 1 wppm. The preferred nitrogen level in the hydrogen feed is less than 1 wppm.

U.S. Patent Application No. 61/047,821 filed on Apr. 25, 2008, the disclosure of which is incorporated in its entirety by reference, discloses a process for making cyclohexylbenzene wherein benzene and hydrogen are contacted with a first catalyst under hydroalkylation conditions sufficient to produce a first effluent stream comprising cyclohexylbenzene, cyclohexane and unreacted benzene. At least part of the first effluent stream comprising cyclohexane and unreacted benzene is then contacted with a second catalyst under dehydrogenation conditions to convert at least part of the cyclohexane to benzene and/or bisphenyl and produce a second effluent stream containing less cyclohexane than the first effluent stream. At least part of the second effluent stream is recycled back to the first contacting (hydroalkylation) step.

In the present process, cyclohexylbenzene is produced by contacting benzene with hydrogen under hydroalkylation conditions in the presence of a hydroalkylation catalyst whereby the benzene undergoes the following reaction (1) to produce cyclohexylbenzene (CHB):

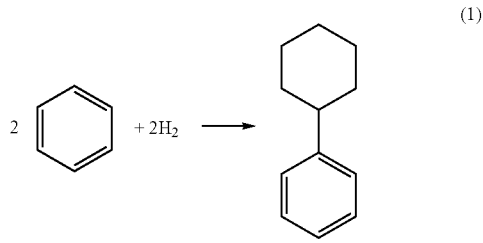

(1)

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 50° C. and about 400° C., such as between about 100° C. and about 250° C., while suitable reaction pressures are between about 100 and about 7,000 kPa, such as between about 500 and about 5,000 kPa. Suitable values for the molar ratio of hydrogen to benzene are between about 0.01 and about 100, more particularly between about 0.15:1 and about 15:1, such as between about 0.4:1 and about 4:1, for example between about 0.4 and about 0.9:1. The benzene weight hourly space velocity is normally from about 0.01 to about 100 hr$^{-1}$.

The catalyst employed in the hydroalkylation reaction is a bifunctional catalyst comprising a molecular sieve with an acid function and a hydrogenation metal. Suitable molecular sieves include zeolite beta, zeolite X, zeolite Y and molecular sieves of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve to produce the catalyst composite. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The hydroalkylation reaction is exothermic, and so the reaction system must take heat management into account. A preferred method is to recycle a portion of the effluent from the hydroalkylation reactor through a cooling heat exchanger, and mix the cooled recycle stream with the feed. It can also be advantageous to have more than one hydroalkylation bed or reactor, and add hydrogen in stages.

The hydroalkylation effluent is conveyed to the dehydrogenation reactor for dehydrogenation. The hydroalkylation effluent may be processed as a single effluent stream or be optionally subjected to one or more separations prior to conveyance to the dehydrogenation reactor to form two or more effluent streams. Such separations can be accomplished by conventional unit operations, such as single-stage flash and/or multi-stage distillation. For instance, one or more $C_6$-rich components (rich in unreacted benzene, byproduct cyclohexane, and methyl cyclopentane) can be separated from heavier CHB-rich product and from lighter compounds. One or more of the $C_6$-rich stream or streams can be recycled to the hydroalkylation reactor to further hydroalkylate unconverted benzene.

Although the hydroalkylation step is highly selective towards cyclohexylbenzene, in addition to the desired monoalkylated species, the effluent from the hydroalkylation reaction will normally contain some dialkylated and other heavy products, as well as unreacted benzene feed. The hydroalkylation effluent is therefore fed to a separation system normally comprising at least two distillation towers. In the first distillation tower, unreacted benzene feed and cyclohexane are recovered from the effluent. The benzene is recycled to the hydroalkylation reactor and the cyclohexane is sent to the dehydrogenation reactor. The bottoms from the first distillation tower are further distilled to recover a purified cyclohexylbenzene product stream. Materials heavier than cyclohexylbenzene may be removed in a purge stream. Optionally, in this step, a polyalkylate stream, comprising at least di-cyclohexylbenzene, may be recovered for feeding to an optional transalkylation step. A heavies stream is still removed at this step and purged from the process. This heavies stream may be a slipstream of the polyalkylate stream, or may be the residue from the purification of a polyalkylate stream, or a combination of both. Generally, the cyclohexylbenzene recovery is accomplished using one or optionally two vacuum distillation towers.

Depending on the amount of dicyclohexylbenzene present in the hydroalkylation effluent, it may be desirable to transalkylate the dicyclohexylbenzene with additional benzene to maximize the production of the desired monoalkylated species. Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y and mordenite. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 $hr^{-1}$ on total feed, and a benzene/dicyclohexylbenzene weight ratio about of 1:1 to about 5:1.

With recycling, methyl cyclopentane conversion levels of about 30% or more, about 70% or more, and even about 99% are possible. Recycling may be carried out continually or continuously depending on the nature of the process.

In addition the effluent from the hydroalkylation reactor will normally contain significant amounts of cyclohexane, since a competing process to the hydroalkylation of benzene to produce cyclohexylbenzene involves the complete saturation of the benzene to produce cyclohexane according to the following reaction (2):

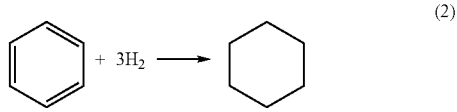
(2)

Even with highly selective hydroalkylation processes such as that described above, it is common to find levels of cyclohexane between 5 wt % and 20 wt % in the reaction product (ignoring unconverted benzene). Since benzene conversions in the hydroalkylation step are typically only 40 to 60%, the $C_6$ product fraction is typically recycled. However, cyclohexane cannot be readily separated from benzene by distillation due to their close boiling points, but cyclohexane can be readily separated from benzene to some extent by dividing the $C_6$ product stream into a cyclohexane-rich stream and a benzene-rich stream. Hence, in an embodiment wherein the cyclohexane is not at least partially separated from the $C_6$ product fraction, the cyclohexane will tend to build up in the $C_6$ recycle stream in the cyclohexylbenzene synthesis step, where it can displace benzene and also lead to further undesirable byproducts. In other embodiments, at least a portion of the cyclohexane may be separated from the benzene to form at least a cyclohexane-rich stream and a benzene-rich stream.

In the present process, the problem of cyclohexane production is minimized by integrating a dehydrogenation step for the cyclohexane into the recycle loop of the hydroalkylation. Thus, in one embodiment, at least a portion of the $C_6$ fraction (typically containing more than 50% benzene and less than 50% cyclohexane) removed from the cyclohexylbenzene product may be fed to a dehydrogenation reactor where the cyclohexane is converted to benzene, with selectivities greater than 90%, such as greater than 96%, for example greater than 99%, according to the following reaction (3):

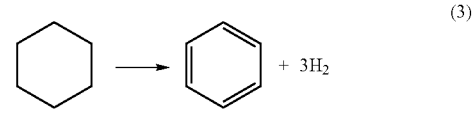
(3)

In another embodiment, the cyclohexane-rich stream may be fed to a dehydrogenation reactor and then recycled back to the hydroalkylation step.

Reaction (3) is of course the inverse of reaction (2). Thus, whereas reaction (2) is favored by conditions of relatively low temperature and high pressure, to drive reaction (3) in the forward direction, thermodynamics demands lower pressure and/or higher temperatures. Thus the cyclohexane dehydrogenation step is typically run under conditions comprising a temperature greater than 300° C., such as between about 330° C. and about 430° C., and a pressure less than 1000 kPa, such as between about 100 and about 500 kpa.

The cyclohexane dehydrogenation is generally conducted in the presence of a catalyst having an active metal function, such as one or more Group VIII metals on a porous non-acidic support. Suitable Group VIII metals include palladium, platinum, nickel, rhodium, ruthenium and combinations thereof. Conveniently, the dehydrogenation metal is combined with one or more other elements, such as potassium, sodium, tin and/or phosphorus, for acid site neutralization and for improving catalyst stability and selectivity. Suitable supports for the dehydrogenation catalyst include aluminum oxide, silicon oxide, titanium oxide, zirconium oxide, activated carbon and combinations thereof. The support typically has a surface area of more than 3 $m^2/g$, such as about 20 to about 500 $m^2/g$. The cyclohexane conversion is typically greater than 50%, such as from about 70 to about 99%.

A gas co-feed to the dehydrogenation reactor is not required, but a hydrogen gas co-feed is preferred to suppress catalyst coking, typically so that the $H_2$/hydrocarbon molar feed ratio is between about 0.5:1 and about 5:1. In fact, in one embodiment, the fresh make-up hydrogen for the overall process is supplied to the cyclohexane dehydrogenation step. The excess and co-produced hydrogen is then compressed and recycled to the hydroalkylation reactor.

Any known reactor configuration can be employed to effect the cyclohexane dehydrogenation, including fixed bed, moving bed and catalytic distillation reactors. Moreover, the reaction can be conducted as a batch or a continuous process.

The dehydrogenation catalyst has an active metal function and some level of acidity. The active metal function takes the form of one or more group VIII metals, preferably on a porous nonacidic support. Useful group VIII metals include Fe, Co, Ni, Ru, Rh, Pd, Os, Ir, and Pt. A preferred dehydrogenation catalyst is Pd. The dehydrogenation catalyst is present in the reaction system in a catalytically effective amount. The catalyst acidity should be less than 1 based on the alpha test scale (alpha test is the n-hexane cracking over any acid catalyst before adding metals at 538° C. and atmospheric pressure).

The linear/branched paraffins can be separated in whole or in part, if desired, from the dehydrogenation effluent stream using conventional distillation techniques. Separation is readily accomplished due to the disparate boiling temperatures of the linear/branched paraffins relative to benzene. If the linear/branched paraffins are separated from the dehydrogenation effluent stream, the remainder of the stream bearing benzene can be recycled to the hydroalkylation step. The benzene can be used to produce additional cyclohexylbenzene.

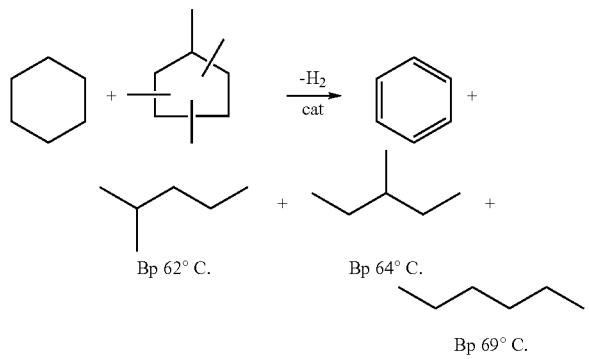

Bp 62° C.   Bp 64° C.

Bp 69° C.

A gas co-feed to the dehydrogenation reactor is not required, but a hydrogen gas co-feed is preferred, with a $H_2$/hydrocarbon molar feed ratio of preferably between 0.5:1 and 5:1. Hydrogen is co-produced with benzene in the dehydrogenation step and can be vented or, more preferably, compressed and recycled to the hydroalkylation reactor.

The following are examples of the present disclosure and are not to be construed as limiting.

EXAMPLES

Catalyst Preparation for Cyclohexylbenzene (CHB) Production

The catalyst was prepared by co-pelletizing a Pd catalyst with an MCM-49 catalyst. The Pd catalyst was prepared by impregnating 5 g (grams) of gamma alumina with a palladium nitrate solution and then calcining the Pd-impregnated alumina at 350° C. for 3 hours in air. The Pd loading on the alumina is 0.3 wt %. The MCM-49 catalyst was prepared by crushing an extrudate that has 80% MCM-49 and 20% alumina to 1/60 inch or finer particles. The Pd/$Al_2O_3$ catalyst was then mixed with the crushed MCM-49/$Al_2O_3$ in the ratio of 1:3 by weight and then pelletized using a hand press under 20,000 pounds per square inch gauge (psig) to form the co-pelletized catalyst. The catalyst was then sized to 60-100 mesh for testing.

Examples 1 to 9

CHB Production Under Various Process Conditions

Eight grams of the catalyst prepared above was charged to a stainless steel fixed-bed micro-reactor. The reactor had a ½-inch inside diameter with a ⅛-inch thermowell in the center throughout the catalyst bed. The catalyst was pre-treated with 100 cubic centimeters per minute (cc/min) of hydrogen for 2 hours (hr) at 300° C. and 1 atmosphere (atm). After cooling to 155° C. in hydrogen, benzene was fed into the reactor through a syringe pump at 60 cc/hour for 1 hr while the reactor pressure was increased to 150 pounds per square inch gauge (psig). Benzene rate was then reduced to 0.52 weight hourly space velocity (WHSV) and hydrogen/benzene molar ratio was adjusted to 1.28. Liquid products were collected in a cold product trap and analyzed off-line. Various test conditions were used to evaluate catalyst performance by varying four process variables. Table 1 shows these process variables and their ranges as well as test results.

TABLE 1

| | Test Condition No. | | | | | | | | |
|---|---|---|---|---|---|---|---|---|---|
| | 1 | 2 | 3 | 4 | 5 | 6 | 7 | 8 | 9 |
| Temperature, ° C. | 150 | 150 | 150 | 150 | 150 | 150 | 150 | 150 | 150 |
| Pressure, psig | 165 | 300 | 300 | 165 | 150 | 150 | 150 | 300 | 600 |
| $H_2$/Benzene Molar Rate | 1.28 | 1.28 | 1.28 | 1.28 | 0.64 | 0.64 | 1.28 | 0.64 | 0.64 |
| Benzene WHSV | 0.52 | 0.52 | 1.05 | 0.26 | 0.52 | 0.26 | 0.52 | 0.52 | 1.05 |
| Benzene Conv., % | 45.7 | 68.5 | 38.1 | 68.5 | 33.6 | 41.9 | 40.6 | 53.5 | 51.6 |
| Hydrogen Conv., % | 48.6 | 75.0 | 30.4 | 98.0 | 86.8 | 97.0 | 30.6 | 97.3 | 96.5 |
| Selectivity, wt % | | | | | | | | | |
| Methylcyclopentane | 0.40 | 0.30 | 0.09 | 0.26 | 0.09 | 0.13 | 0.27 | 0.18 | 0.11 |
| Cyclohexane | 4.0 | 6.1 | 5.1 | 6.0 | 4.2 | 5.0 | 3.9 | 5.9 | 10.4 |
| CHB[a] | 63.9 | 58.6 | 71.8 | 58.4 | 75.8 | 72.8 | 61.5 | 69.1 | 67.5 |
| Methylcyclopentylbenzene | 2.5 | 2.2 | 2.0 | 2.3 | 2.1 | 2.4 | 2.5 | 2.3 | 1.9 |
| DCHB[b] | 24.5 | 27.6 | 18.2 | 27.3 | 15.5 | 16.6 | 26.4 | 19.4 | 17.2 |
| Methylcyclopentyl-cyclohexylbenzene | 3.1 | 3.1 | 2.2 | 3.6 | 1.8 | 2.4 | 3.3 | 2.2 | 2.3 |
| Others | 1.4 | 2.0 | 0.6 | 2.1 | 0.4 | 0.4 | 1.9 | 0.7 | 0.5 |
| Sum | 100 | 100 | 100 | 100 | 100 | 100 | 100 | 100 | 100 |
| CHB + DCHB sel., % | 88.4 | 86.2 | 90.0 | 85.6 | 91.3 | 89.4 | 88.0 | 88.6 | 84.7 |
| Product Yield, % | | | | | | | | | |
| Cyclohexane | 1.8 | 3.0 | 2.5 | 2.9 | 2.0 | 2.4 | 1.9 | 2.9 | 5.1 |
| CHB[a] | 29.2 | 28.6 | 35.0 | 28.4 | 37.0 | 35.5 | 30.0 | 33.7 | 32.9 |
| DCHB[b] | 11.2 | 13.5 | 8.9 | 13.3 | 7.5 | 8.1 | 12.9 | 9.5 | 8.4 |
| CHB + DCHB | 40.4 | 42.0 | 43.9 | 41.7 | 44.5 | 43.6 | 42.9 | 43.2 | 41.3 |

[a]CHB: Cyclohexylbenzene.
[b]DCHB: dicyclohexylbenzene.

Examples 10 and 11

Cyclohexane/Methyl Cyclopentane Dehydrogenation

The reactor used in the experiments is stainless steel with dimensions of 22 inches (in.) long×⅜ in. outside diameter (o.d.)×0.035 in. wall thickness. A piece of 8¾ in. long×¼ in. o.d stainless steel tubing was used in the bottom of the reactor as a spacer to position and support the catalyst in the isothermal zone of the furnace. A ¼ in. plug of glass wool was placed at the top of the spacer to keep the catalyst in place. A ⅛ in. thermo-well was placed in the catalyst bed, long enough to accommodate temperature scanning throughout the catalyst bed.

The catalyst was pressed into pellets then crushed and sized to 20 to 40 US sieve mesh. Typically 2.5 grams (g) of the catalyst pre sized to 20 to 40 mesh was diluted with quartz chips of the same size to a volume of 5.5 cc. The mixed portion of catalyst was then loaded into the reactor from the top. The catalyst bed typically was 12.5 cm. in length. A ¼ in. plug of glass wool was placed at the top of the catalyst bed to separate quartz chips from the catalyst. The remaining void space at the top of the reactor was filled with quartz chips. The reactor was installed in the furnace with the catalyst bed in the middle of the furnace at the pre marked isothermal zone. The reactor was then pressure and leak tested with hydrogen typically at 300 psig.

The catalyst was pre-conditioned in situ; heated to 300° C. with $H_2$ flow at 50 cc/min and held for 2 hrs. Then the feed was introduced. A 500 cc ISCO syringe pump was used to introduce the 95% cyclohexane 5% methyl cyclopentane mixture to a vaporizer then through heated lines to the reactor. A Brooks mass flow controller was used for hydrogen feed measurements. A research control valve was used to control the reactor pressure typically at 50 psig. GC analyses were taken to verify feed composition. A feed containing 95% cyclohexane and 5% methyl cyclopentane was flown through the catalyst bed held at a reaction temperature of 300° C. to 500° C. at a WHSV of 2 and a pressure of 50 psig. The products exiting the reactor through heated lines routed to a Hewlett and Packard 5890 gas chromatograph with FID (flame ionization detector) and TCD (thermal conductive detector) detectors for analysis. A J&W Scientific DB-1 capillary column 60 m (meters)×0.32 mm (millimeters)×1.0 micron film thickness was used for the analysis of hydrocarbon products. A Supelco Carboxen 1000, ⅛ in.×30 ft (feet) s.s. stainless steel column was used to analyze fixed gases. Analyses were taken typically at 3-hour intervals.

The GC analysis ramp program was set to the following: −30° C. for 3 minutes (min.); 5° C./min, to 120° C., held 0 min, 20° C./min, to 200° C. held 22 min, and 30° C./min, to 270° C. held to the end. Total analysis time was 75 min.

A time-on-stream (TOS) profile is shown in Tables 2 and 3 and FIG. 1. Two different catalysts were used, 0.3%/$Al_2O_3$ from Akzo and PtKL (prepared by the method described in WO 9106616 A2. The catalysts were tested at different temperatures and different T.O.S for stability.

Table 2 and 3 show cyclohexane and methyl cyclopentane conversion and the selectivity to products produced using the 0.3%/$Al_2O_3$ catalyst.

TABLE 2

| T.O.S. (hours) | Temperature (° C.) | CH Conversion (wt %) | Benzene Selectivity (wt %) |
|---|---|---|---|
| 4.5 | 375 | 93 | 99.8 |
| 6 | 400 | 98.3 | 99.8 |
| 10 | 423 | 99.4 | 99.7 |
| 10 | 448 | 99.3 | 99.1 |

TABLE 3

| T.O.S. (hours) | Temperature (° C.) | MCP Conversion (wt %) | 2-methyl pentane Selectivity (wt %) | 3-methyl pentane Selectivity (wt %) | n-hexane Selectivity (wt %) |
|---|---|---|---|---|---|
| 4.5 | 375 | 12.4 | 51 | 25.6 | 21 |
| 6 | 400 | 34 | 51 | 29 | 18 |
| 10 | 423 | 55 | 45 | 29 | 20 |
| 10 | 448 | 62 | 44 | 32 | 29 |

Referring to Table 2 and FIG. 1, no MCP conversion was observed at 350° C. 70% of the CH was converted to benzene. The selectivity was 99.8%. The catalyst remained stable after 48 hours at 350° C. At 400° C., the CH conversion was 98% and the selectivity to benzene was 99.8%. The main by-product is biphenyl. At 400° C., MCP conversion was 35%. No catalyst deactivation was observed at 400° C. MCP was converted to 2-methyl pentane, 3-methyl pentane and hexane. FIG. 1 shows that the catalyst remains stable for more than 150 hrs on stream.

The effect of increased reaction temperature on MCP conversion was evaluated. The data are shown in FIG. 1. The data show that 0.3% Pt/Akzo deactivates very fast at temperature >450° C., while the catalyst Pt/KL remains stable, active, and selective at temperature >450° C. At a temperature of 500° C., the CH and MCP conversions are about 100%.

Applicants have attempted to disclose all embodiments and applications of the disclosed subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

All patents, test procedures, and other documents cited herein, including priority documents, are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

What is claimed is:

1. A process for making cyclohexylbenzene, comprising:
    (a) contacting benzene and hydrogen in the presence of a first catalyst under hydroalkylation conditions sufficient to form a first effluent stream having cyclohexylbenzene, cyclohexane, methyl cyclopentane, and unreacted benzene;
    (b) supplying at least part of said first effluent stream to a first separation system to divide said first effluent stream part into a cyclohexane/methylcyclopentane-rich stream, a cyclohexane-rich stream, a benzene-rich stream, and a dicyclohexyl benzene-rich stream;
    (c) recycling at least part of the benzene-rich stream to the contacting step (a);
    (d) contacting the cyclohexane/methylcyclopentane-rich stream with a second catalyst that catalyzes dehydrogenation and exhibits low acidity under conditions sufficient to convert at least a portion of the cyclohexane to benzene and at least a portion of the methylcyclopentane to linear and/or branched paraffins to form a second effluent stream; and (e) recycling at least part of the second effluent stream to the contacting step (a).

2. The process of claim 1 further including supplying the second effluent stream to a second separation system to form a benzene-rich stream and a paraffins-rich stream and recycling the benzene-rich stream to the contacting step (a).

3. The process of claim 1, wherein said hydroalkylation conditions include a temperature of 50 to 400° C., a pressure of 100 to 7000 kpa, a weight hourly space velocity of 0.01 to 100 hr$^{-1}$ and a benzene to hydrogen molar ratio of 0.01 to 100.

4. The process of claim 1, wherein said dehydrogenation conditions comprise a temperature between 330° C. and 500° C. and a pressure between 100 and 1000 kPa.

5. The process of claim 1, wherein the first catalyst is a molecular sieve and a hydrogenation metal.

6. The process of claim 1, wherein the first catalyst is selected from Pd, Pt, Rh, Ru, Co, Ni, Ru, Sn, and Zn.

7. The process of claim 1, wherein the first catalyst is Pd.

8. The process of claim 1, wherein the first separation system further separates a dicyclohexylbenzene-rich stream from the first effluent stream and the process further comprises contacting the dicyclohexylbenzene-rich stream with further benzene in the presence of a transalkylation catalysts to convert the dicyclohexylbenzene to additional cyclohexylbenzene.

9. The process of claim 1, wherein the first catalyst is a metal or compound thereof of Group 8 of the Periodic Table on a porous, non-acidic support.

* * * * *